(12) United States Patent
Cahana et al.

(10) Patent No.: US 9,441,278 B2
(45) Date of Patent: Sep. 13, 2016

(54) GENOTYPING METHOD FOR USE IN CATTLE TRACEABILITY AND MEANS THEREOF

(75) Inventors: Aviv Cahana, Moshav Sitria (IL); Andrey Shirak, Petach Tikva (IL); Baruch Karniol, Bat Yam (IL); Yitzchak Skalsky, Nitzan M.P. Evtach (IL); Joel Ira Weller, Rehovot (IL); Micha Ron, Nes Tziona (IL); Eyal Seroussi, Sha'arei Tikva (IL)

(73) Assignees: BACTOCHEM LTD., Nes Ziona (IL); STATE OF ISRAEL, MINISTRY OF AGRICULTURE AND RURAL DEVELOPMENT, A.R.O.—VOLCANI CENTER, Beit Dagan (IL)

( * ) Notice: Subject to any disclaimer, the term of this patent is extended or adjusted under 35 U.S.C. 154(b) by 1196 days.

(21) Appl. No.: 13/000,314

(22) PCT Filed: Jun. 14, 2009

(86) PCT No.: PCT/IL2009/000588
§ 371 (c)(1),
(2), (4) Date: Dec. 20, 2010

(87) PCT Pub. No.: WO2009/153779
PCT Pub. Date: Dec. 23, 2009

(65) Prior Publication Data
US 2011/0092379 A1      Apr. 21, 2011

Related U.S. Application Data

(60) Provisional application No. 61/073,780, filed on Jun. 19, 2008.

(51) Int. Cl.
C12P 19/34       (2006.01)
C12Q 1/68        (2006.01)

(52) U.S. Cl.
CPC .......... C12Q 1/6888 (2013.01); C12Q 1/6827 (2013.01); *C12Q 2600/156* (2013.01); *C12Q 2600/16* (2013.01)

(58) Field of Classification Search
USPC ........................ 435/6.12, 91.2; 536/24.33
See application file for complete search history.

(56) References Cited

U.S. PATENT DOCUMENTS 7,807,361 B2 * 10/2010 Khatib ........................ 435/6.1
2006/0172329 A1 * 8/2006 Taylor et al. ................. 435/6

FOREIGN PATENT DOCUMENTS

DE     102 12 560 A1    10/2003
WO    2005/073408 A2    8/2005
WO    2006/029256 A2    3/2006

OTHER PUBLICATIONS

Karniol, B. et al., "Development of a 25-plex SNP assay for traceability in cattle", Animal Genetics, 40(3):353-356 (Mar. 9, 2009).
Ragoussis, J. et al., "Matrix-Assisted Laser Desorption/Ionisation, Time-of-Flight Mass Spectrometry in Genomics Research", PLoS Genetics, 2(7):920-929 (Jul. 2006).
Rohrer, G. A. et al., "Single nucleotide polymorphisms for pig identification and parentage exclusion", Animal Genetics, 38:253-258 (2007).
Sanchez, Juan J. et al., "Typing of Y Chromosome SNPs with Multiplex PCR Methods", Methods in Molecular Biology, 297:209-228 (Jan. 1, 2005).
Shirak, Andrey et al., "Traceability system for cattle based on genotyping of 25-plex using SNaPshot method", (2008).
Werner, F. A. et al., "Detection and characterization of SNPs useful for identity control and parentage testing in major European dairy breeds", Animal Genetics, 35(1):44-49 (Feb. 2004).
Latham, K. et al., "The Sequienomm Massarray Technology as a High Through-Put SNP Genotyping System", International Journal of Immunogenetics 33, British Society for Histocompatibility and Immunogenetics, Abstracts of Papers Presented at the Seventeenth Annual BSHI Conference, Sheffield, Sep. 13-15, 2005, Abstract No. 5.01.
Secondary Guidelines for Development of National Farm Animal Genetic Resources Management Plans, Measurement of Domestic Animal Diversity (MoDAD): Recommended Microsatellite Markers, New Microsatellite marker sets—Recommendations of joint ISAG/FAO Standing Committee (2004).
International Search Report for PCT/IL2009/000588 dated Feb. 3, 2010.
Written Opinion for PCT/IL2009/000588 dated Feb. 3, 2010.
International Preliminary Report on Patentability for PCT/IL2009/000588 dated Aug. 18, 2010.
"Agricultural & Biosystems Engineering for a Sustainable World," Final Program for 2008 International Conference on Agricultural Engineering (AgEng 2008), Jun. 23-25, 2008, Hersonissos, Crete—Greece, pp. 1-52 (See p. 12).

* cited by examiner

*Primary Examiner* — Kenneth Horlick

(57) ABSTRACT

The invention discloses means and methods for genotyping an individual head of cattle. Individual's DNA is genotyped utilizing the herein defined PCR SNaP-shot protocol. The protocol comprises two PCR steps where the first step (PCR1) includes adding primers (SEQ ID No. 1-30) and/or primers extended at their 5' end with a common 10 base motif (ACGTTGGATG) to the PCR1 reaction. The second step (PCR2) includes adding extension primers (SEQ ID No. 31-45), and/or primers adjacent to corresponding specific SNPs. Further steps include producing amplicons from a PCR1 mixture comprising template DNA and the first primer set to yield PCR1 products, using PCR1 products as templates to a set of extension primers to yield PCR2 products. Size and color separation is achieved by adding tails of different lengths to the PCR2 primers. PCR2 products are separated and the results compared with SNP profiles from the databank to obtain matching.

17 Claims, 7 Drawing Sheets

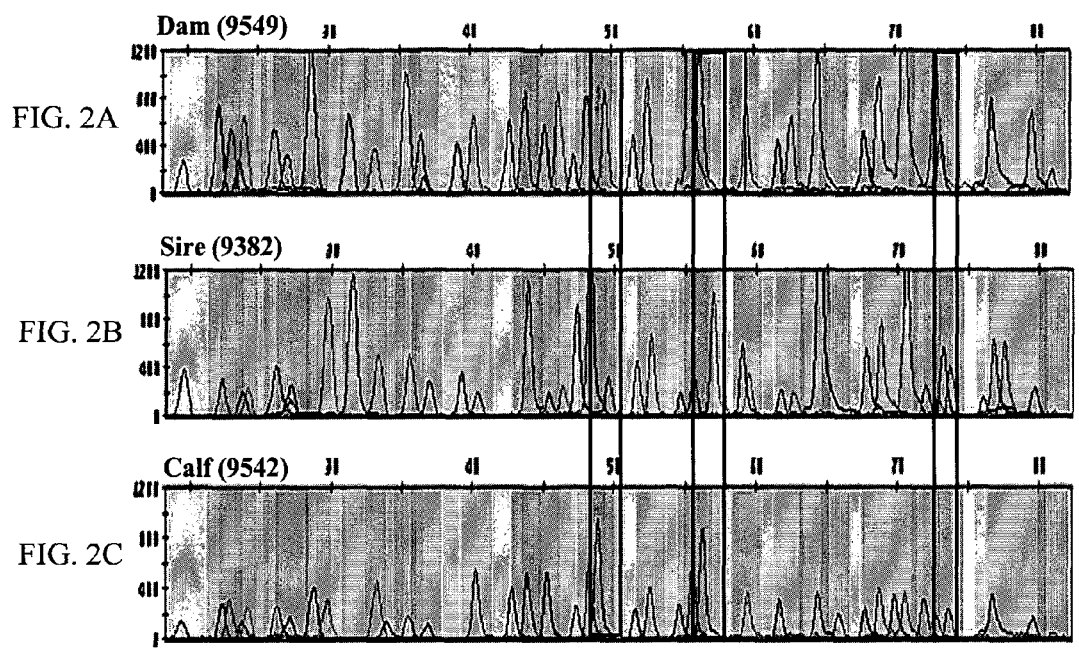

FIG. 3A
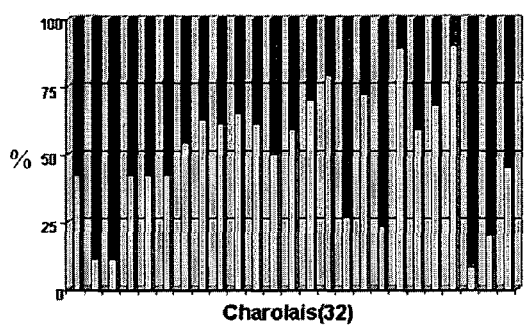
FIG. 3B
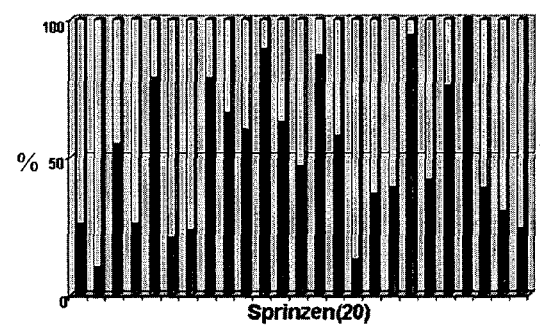
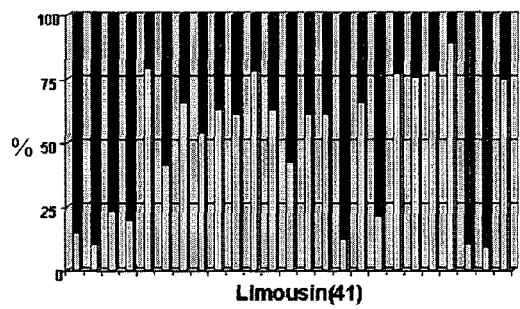
FIG. 3C
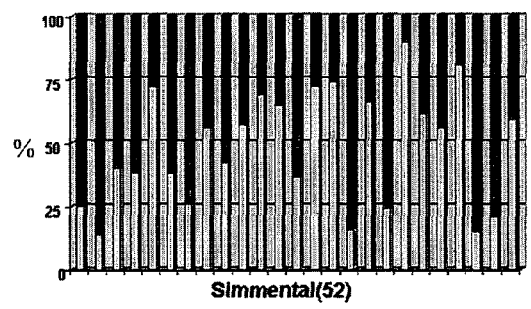
FIG. 3D

PDT

FDT

OUR UNIQUELY DESIGNED SOFTWARE ENABLES YOU

| #SNP | PCR1 Forward | | PCR1 Reverse | | SNaPshot PCR2 Extension | |
|---|---|---|---|---|---|---|
| | SeqID | Sequence | SeqID | Sequence | SeqID | Sequence |
| SNP11 | 1 | ACGTTGGATGCTTTGTGACCTCATGGACTC | 16 | ACGTTGGATGAGTGTCACTGACTCAAATGG | 31 | GACCTTCACCACCTCC |
| SNP13 | 2 | ACGTTGGATGCACTAAGTGGAATGAGCCTG | 17 | ACGTTGGATGGCTCATAGGTTGTAGTCAAG | 32 | AGTTGAATGAGCCTGAATTGTATATC |
| SNP15 | 3 | ACGTTGGATGCCAAACCTCTTCTCAGAATC | 18 | ACGTTGGATGGGCCTTGTAATCTTATATTGC | 33 | ACTTCAAAGGAGCCTTC |
| SNP16 | 4 | ACGTTGGATGACCCACTCTACTCTCACTTC | 19 | ACGTTGGATGGAAGACCTGGAGGGATTTTG | 34 | A(14)CA(23)CA(23)GGAAACAGATGCTCAACTCT |
| SNP17 | 5 | ACGTTGGATGGCAATTGTCAGCAACACCAG | 20 | ACGTTGGATGAGATCATGCTTTCCCTGAAG | 35 | A(14)CA(23)CA(12)GGGGAAGACATGGAACAGATTCT |
| SNP18 | 6 | ACGTTGGATGTGGATTTTCAGCAACCCTTG | 21 | ACGTTGGATGATTCTGCAGCCAATGTGACC | 36 | A(28)CCCGTCAGCAACCCTTGGGTAGA |
| SNP20 | 7 | ACGTTGGATGAAGCCCCTCCAGCATAAAAG | 22 | ACGTTGGATGCTTTCCGTTCTGCCAATGTC | 37 | A(14)CA(23)CA(18)TAGTCTTCTGTCATATGCAAA |
| SNP21 | 8 | ACGTTGGATGATCATGCAGTGAGATGACCC | 23 | ACGTTGGATGTTCAGGAAGCCCTGCAAGAG | 38 | A(45)GATGACCCCGTGGAGCTT |
| SNP26 | 9 | ACGTTGGATGTTCTTTGGCGTTCCCACTTC | 24 | ACGTTGGATGCAAATAGATTCCAAGAAGGC | 39 | A(14)CA(23)CA(30)CCCACTTCTCCCTTAAT |
| SNP27 | 10 | ACGTTGGATGAGTAGCTGAACTCATGGTGC | 25 | ACGTTGGATGCTAAACCGTACAATACTGGC | 40 | A(13)CA(24)CA(18)TGCTTTAGTGAGGACA |
| SNP28 | 11 | ACGTTGGATGAACAAAAGGCCTCCACATCC | 26 | ACGTTGGATGTTTGGTGCCAGTTGAAAGCC | 41 | ACCTGCTCCCTGTAAGGTCTTTTAGAT |
| SNP2 | 12 | ACGTTGGATGCAACCTCCAAAACCCTCAAG | 27 | ACGTTGGATGTTTCCAGGTCTCAGTCTGGG | 42 | A(19)TTCAACCCTCAAGGCAACAA |
| SNP30 | 13 | ACGTTGGATGGGCAGAATTGCCATAGTGGG | 28 | ACGTTGGATGCAATCACAGCTATTGAGCCC | 43 | A(40)CCATAGTGGGCATCAAGA |
| SNP31 | 14 | ACGTTGGATGGATGGATAGTGTGCCCATTC | 29 | ACGTTGGATGAGTCCAGGGATGGATATTAC | 44 | A(24)CA(22)GGCCCATTCCTTTCATTTC |
| SNP32 | 15 | ACGTTGGATGACACACCATTTAGTCACAT | 30 | ACGTTGGATGGTGTGCTTGTATATGTTCGTG | 45 | A(20)CA(18)CACCATTTAGTCACATATACAC |

FIG. 7A

| #SNP | Map | Allele A | Bin A (bp) | Allele B | Bin B (bp) |
|---|---|---|---|---|---|
| SNP11 | chr20:34,5 | SNP11C | 22.7-24.95 | SNP11T | 25.3-27.87 |
| SNP13 | chr9:33,8 | SNP13G | 28.3-29.91 | SNP13A | 29-31 |
| SNP15 | chr9:55,2 | SNP15G | 21.3-23.3 | SNP15A | 23.2-25.56 |
| SNP16 | chr20:58,3 | SNP16C | 75.6-77.6 | SNP16T | 76.4-78.4 |
| SNP17 | chr6:43,7 | SNP17C | 68.6-70.6 | SNP17T | 69.6-71.3 |
| SNP18 | chr3:28,7 | SNP18G | 48-50 | SNP18A | 48.6-50.6 |
| SNP20 | chr1:8,2 | SNP20C | 72-74 | SNP20T | 72.6-74.6 |
| SNP21 | chr19:27,5 | SNP21C | 57.6-59.6 | SNP21T | 58.3-60.3 |
| SNP26 | chr25:35,3 | SNP26G | 79.5-80.5 | SNP26T | 80-82 |
| SNP27 | chr1:142,3 | SNP27C | 66.5-68.5 | SNP27T | 67.5-69.5 |
| SNP28 | chr28:25,1 | SNP28G | 30.8-33.79 | SNP28A | 32.5-35.06 |
| SNP2 | chr1:137 | SNP2G | 35.7-37.7 | SNP2C | 36.1-38.1 |
| SNP30 | chr10:8,5 | SNP30C | 53.6-55.6 | SNP30T | 54.5-56.5 |
| SNP31 | chr8:48,8 | SNP31C | 60.4-62.4 | SNP31T | 61.3-63.3 |
| SNP32 | chr2:105.7 | SNP32G | 54.9-56.9 | SNP32A | 55.6-57.6 |

FIG. 7B

SEQUENCE LISTING

```
<160> NUMBER OF SEQ ID NOS: 45

<210> SEQ ID NO 1
<211> LENGTH: 33
<212> TYPE: DNA
<213> ORGANISM: cattle

<400> SEQUENCE: 1
acgttggatg acactttgtg acctcatgga ctc                          33

<210> SEQ ID NO 2
<211> LENGTH: 30
<212> TYPE: DNA
<213> ORGANISM: cattle

<400> SEQUENCE: 2
acgttggatg cactaagtgg aatgagcctg                              30

<210> SEQ ID NO 3
<211> LENGTH: 30
<212> TYPE: DNA
<213> ORGANISM: cattle

<400> SEQUENCE: 3
acgttggatg ccaaacctct tctcagaatc                              30

<210> SEQ ID NO 4
<211> LENGTH: 30
<212> TYPE: DNA
<213> ORGANISM: cattle

<400> SEQUENCE: 4
acgttggatg acccactcta ctctcacttc                              30

<210> SEQ ID NO 5
<211> LENGTH: 30
<212> TYPE: DNA
<213> ORGANISM: cattle
```

```
<400> SEQUENCE: 5
acgttggatg gcaattgtca gcaacaccag                                              30

<210> SEQ ID NO 6
<211> LENGTH: 30
<212> TYPE: DNA
<213> ORGANISM: cattle

<400> SEQUENCE: 6
acgttggatg tggattttca gcaaccttg                                               30

<210> SEQ ID NO 7
<211> LENGTH: 30
<212> TYPE: DNA
<213> ORGANISM: cattle

<400> SEQUENCE: 7
acgttggatg aagcccctcc agcataaaag                                              30

<210> SEQ ID NO 8
<211> LENGTH: 30
<212> TYPE: DNA
<213> ORGANISM: cattle

<400> SEQUENCE: 8
acgttggatg atcatgcagt gagatgaccc                                              30

<210> SEQ ID NO 9
<211> LENGTH: 30
<212> TYPE: DNA
<213> ORGANISM: cattle

<400> SEQUENCE: 9
acgttggatg ttctttggcg ttcccacttc                                              30

<210> SEQ ID NO 10
<211> LENGTH: 30
<212> TYPE: DNA
<213> ORGANISM: cattle

<400> SEQUENCE: 10
acgttggatg agtagctgaa ctcatggtgc                                              30

<210> SEQ ID NO 11
<211> LENGTH: 30
<212> TYPE: DNA
<213> ORGANISM: cattle

<400> SEQUENCE: 11
acgttggatg aacaaaaggc ctccacatcc                                              30

<210> SEQ ID NO 12
<211> LENGTH: 30
<212> TYPE: DNA
<213> ORGANISM: cattle

<400> SEQUENCE: 12
acgttggatg caacctccaa aaccctcaag                                              30

<210> SEQ ID NO 13
<211> LENGTH: 30
<212> TYPE: DNA
```

```
<213> ORGANISM: cattle

<400> SEQUENCE: 13
acgttggatg ggcagaattg ccatagtggg                                    30

<210> SEQ ID NO 14
<211> LENGTH: 30
<212> TYPE: DNA
<213> ORGANISM: cattle

<400> SEQUENCE: 14
acgttggatg gatggatagt gtgcccattc                                    30

<210> SEQ ID NO 15
<211> LENGTH: 29
<212> TYPE: DNA
<213> ORGANISM: cattle

<400> SEQUENCE: 15
acgttggatg acacaccatt tagtcacat                                     29

<210> SEQ ID NO 16
<211> LENGTH: 30
<212> TYPE: DNA
<213> ORGANISM: cattle

<400> SEQUENCE: 16
acgttggatg agtgtcactg actcaaatgg                                    30

<210> SEQ ID NO 17
<211> LENGTH: 30
<212> TYPE: DNA
<213> ORGANISM: cattle

<400> SEQUENCE: 17
acgttggatg gctcataggt tgtagtcaag                                    30

<210> SEQ ID NO 18
<211> LENGTH: 31
<212> TYPE: DNA
<213> ORGANISM: cattle

<400> SEQUENCE: 18
acgttggatg ggccttgtaa tcttatattg c                                  31

<210> SEQ ID NO 19
<211> LENGTH: 30
<212> TYPE: DNA
<213> ORGANISM: cattle

<400> SEQUENCE: 19
acgttggatg gaagacctgg agggattttg                                    30

<210> SEQ ID NO 20
<211> LENGTH: 30
<212> TYPE: DNA
<213> ORGANISM: cattle

<400> SEQUENCE: 20
acgttggatg agatcatgct ttccctgaag                                    30

<210> SEQ ID NO 21
<211> LENGTH: 30
```

```
<212> TYPE: DNA
<213> ORGANISM: cattle

<400> SEQUENCE: 21
acgttggatg attctgcagc caatgtgacc                                    30

<210> SEQ ID NO 22
<211> LENGTH: 30
<212> TYPE: DNA
<213> ORGANISM: cattle

<400> SEQUENCE: 22
acgttggatg ctttccgttc tgccaatgtc                                    30

<210> SEQ ID NO 23
<211> LENGTH: 30
<212> TYPE: DNA
<213> ORGANISM: cattle

<400> SEQUENCE: 23
acgttggatg ttcaggaagc cctgcaagag                                    30

<210> SEQ ID NO 24
<211> LENGTH: 30
<212> TYPE: DNA
<213> ORGANISM: cattle

<400> SEQUENCE: 24
acgttggatg caaatagatt ccaagaaggc                                    30

<210> SEQ ID NO 25
<211> LENGTH: 30
<212> TYPE: DNA
<213> ORGANISM: cattle

<400> SEQUENCE: 25
acgttggatg ctaaaccgta caatactggc                                    30

<210> SEQ ID NO 26
<211> LENGTH: 30
<212> TYPE: DNA
<213> ORGANISM: cattle

<400> SEQUENCE: 26
acgttggatg tttggtgcca gttgaaagcc                                    30

<210> SEQ ID NO 27
<211> LENGTH: 30
<212> TYPE: DNA
<213> ORGANISM: cattle

<400> SEQUENCE: 27
acgttggatg tttccaggtc tcagtctggg                                    30

<210> SEQ ID NO 28
<211> LENGTH: 30
<212> TYPE: DNA
<213> ORGANISM: cattle

<400> SEQUENCE: 28
acgttggatg caatcacagc tattgagccc                                    30

<210> SEQ ID NO 29
```

```
-continued

<211> LENGTH: 30
<212> TYPE: DNA
<213> ORGANISM: cattle

<400> SEQUENCE: 29
acgttggatg agtccaggga tggatattac                                    30

<210> SEQ ID NO 30
<211> LENGTH: 31
<212> TYPE: DNA
<213> ORGANISM: cattle

<400> SEQUENCE: 30
acgttggatg gtgtgcttgt atatgttcgt g                                  31

<210> SEQ ID NO 31
<211> LENGTH: 16
<212> TYPE: DNA
<213> ORGANISM: cattle

<400> SEQUENCE: 31
gaccttcacc acctcc                                                   16

<210> SEQ ID NO 32
<211> LENGTH: 26
<212> TYPE: DNA
<213> ORGANISM: cattle

<400> SEQUENCE: 32
agttgaatga gcctgaattg tatatc                                        26

<210> SEQ ID NO 33
<211> LENGTH: 17
<212> TYPE: DNA
<213> ORGANISM: cattle

<400> SEQUENCE: 33
acttcaaagg agccttc                                                  17

<210> SEQ ID NO 34
<211> LENGTH: 82
<212> TYPE: DNA
<213> ORGANISM: cattle

<400> SEQUENCE: 34
aaaaaaaaaa aaacaaaaa aaaaaaaaaa aaaaaaaca aaaaaaaaa aaaaaaaaa       60 aaggaaacag atgctcaact ct                                            82

<210> SEQ ID NO 35
<211> LENGTH: 74
<212> TYPE: DNA
<213> ORGANISM: cattle

<400> SEQUENCE: 35
aaaaaaaaaa aaacaaaaa aaaaaaaaaa aaaaaaaca aaaaaaaaa agggggaagac      60 atggaacaga ttct                                                     74

<210> SEQ ID NO 36
<211> LENGTH: 51
<212> TYPE: DNA
<213> ORGANISM: cattle

<400> SEQUENCE: 36
```

```
aaaaaaaaaa aaaaaaaaaa aaaaaaaacc cgtcagcaac ccttgggtag a        51

<210> SEQ ID NO 37
<211> LENGTH: 78
<212> TYPE: DNA
<213> ORGANISM: cattle

<400> SEQUENCE: 37
aaaaaaaaaa aaacaaaaa aaaaaaaaaa aaaaaaaaca aaaaaaaaaa aaaaaaatag    60
tcttctgtca tatgcaaa                                                78

<210> SEQ ID NO 38
<211> LENGTH: 63
<212> TYPE: DNA
<213> ORGANISM: cattle

<400> SEQUENCE: 38
aaaaaaaaaa aaaaaaaaaa aaaaaaaaaa aaaaaaaaaa aaaagatga ccccgtggag   60 ctt                                                                63

<210> SEQ ID NO 39
<211> LENGTH: 86
<212> TYPE: DNA
<213> ORGANISM: cattle

<400> SEQUENCE: 39
aaaaaaaaaa aaacaaaaa aaaaaaaaaa aaaaaaaaca aaaaaaaaaa aaaaaaaaaa    60
aaaaaaaaac ccacttctcc cttaat                                       86

<210> SEQ ID NO 40
<211> LENGTH: 73
<212> TYPE: DNA
<213> ORGANISM: cattle

<400> SEQUENCE: 40
aaaaaaaaaa aaacaaaaa aaaaaaaaaa aaaaaaaaca aaaaaaaaaa aaaaaatgc    60 tttagtgagg aca                                                     73

<210> SEQ ID NO 41
<211> LENGTH: 27
<212> TYPE: DNA
<213> ORGANISM: cattle

<400> SEQUENCE: 41
acctgctccc tgtaaggtct tttagat                                      27

<210> SEQ ID NO 42
<211> LENGTH: 39
<212> TYPE: DNA
<213> ORGANISM: cattle

<400> SEQUENCE: 42
aaaaaaaaaa aaaaaaaaat tcaaccctca aggcaacaa                         39

<210> SEQ ID NO 43
<211> LENGTH: 58
<212> TYPE: DNA
<213> ORGANISM: cattle

<400> SEQUENCE: 43
```

```
aaaaaaaaaa aaaaaaaaaa aaaaaaaaaa aaaaaaaaaa ccatagtggg catcaaga        58

<210> SEQ ID NO 44
<211> LENGTH: 66
<212> TYPE: DNA
<213> ORGANISM: cattle

<400> SEQUENCE: 44
aaaaaaaaaa aaaaaaaaaa aaaacaaaaa aaaaaaaaaa aaaaaaggc ccattcctttt      60 catttc                                                                 66

<210> SEQ ID NO 45
<211> LENGTH: 61
<212> TYPE: DNA
<213> ORGANISM: cattle

<400> SEQUENCE: 45
aaaaaaaaaa aaaaaaaaaa caaaaaaaaa aaaaaaaaac accatttagt cacatataca      60
c                                                                      61
```

GENOTYPING METHOD FOR USE IN CATTLE TRACEABILITY AND MEANS THEREOF

RELATED APPLICATION DATA

This application is the U.S. National Stage of PCT/IL2009/000588, filed Jun. 14, 2009, which claims priority to U.S. Provisional Patent Application No. 61/073,780, filed Jun. 19, 2008, the contents of each of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 7,288 byte ASCII (text) file named "Seq_List" created on Dec. 20, 2010.

FIELD OF THE INVENTION

The invention generally relates to genotyping methods and means and more specifically, the invention relates to traceability of livestock and food products.

BACKGROUND OF THE INVENTION

The increased awareness in most western countries of the importance of animal traceability is driven by factors such as globalisation, diseases such as foot and mouth and BSE and advances in science and technology. Animal identification enables tracking and isolating disease outbreaks quickly, helps safeguard our food supply, protects exported markets, helps to deter thefts, and is a tool to improve management of the supply chain. Traceability schemes are thus of interest to farmers, veterinarians, meat processors, retailers and consumers, as well as government officials. Indeed most western governments these days require some level of livestock traceability and meat-consumers in different countries have shown varying levels of willingness-to-pay for traceability programs.

Today, DNA-tagging is recognised to be the best approach for testing and identifying the nature and source of all products made from animals until consumption. However, at present, genetic traceability is a cumbersome technique requiring considerable laboratory skills, and is not suited for applying to a large animal population.

Easy to use traceability schemes based on DNA identification systems would be especially useful if they could be applied at different levels of breadth, depth and precision. In Europe, Israel, US, Canada, Australia, Brazil, Argentina, and Japan traceability schemes of varying types are in use, but they are all limited in their usefulness and accuracy, because they are not based on an efficient easy to use DNA identification system.

Triggered by the BSE scandal, EU-wide compulsory identification of farm animals was introduced, in which after birth, animals are provided with two numbered ear-tags (including electronic RFID tags) that allow their identification. The abattoir can determine from which farm the animal originated by checking the ear-number. However these ear-tags are not safe from forgery and this identification is removed when the animal is slaughtered. Modern detection methods (PCR, sequencing, etc) can determine, even from very small tissue samples, whether or not they derive from a particular individual. Traceability systems are being implemented in beef producing and trading countries. The systems 'breadth, depth, and precision, depends mostly on the difficulties of tissue sampling, extraction, analysis and storage.

Tissue/DNA sampling—Blood samples are usually collected by the veterinarian and analysed. However for larger animal populations this is too labour-intensive and it is not practicable from an economic point of view. Agrobiogen has patented an ear-tagging approach, which automatically takes a small sample of tissue once the tag is locked into the animal's ear. The tissue is contained in a bar-coded chamber, which is self-sealing and contains a desiccant, which after contact mummifies the tissue and preserves DNA.

DNA extraction—The current conventional method for DNA sample preparation involves several steps, which are time- and cost-consuming. Nexttec, a sister company of Agrobiogen has patented a new column system (PCT/EP00/00117), which is the complete reversal of the usual separation process: instead of binding DNA, washing away all undesired compounds and finally eluting the DNA, unwanted components with enzyme-inhibiting properties are bound to the chromatographic sorbent, while the desired DNA passes through in one single step.

DNA analyses—The only commercial cattle parentage typing system (StockMarks, Applied Biosystems) is based on microsatellite markers. SNPs, which are characterized by digital scores that are efficient for automatic genotyping, are likely to replace the microsatellite genotyping. There are SNP genotyping platforms. There are virtually millions of SNPs in the genome, but it is only those with a bi-allelic distribution (i.e. at least 90:10) which are considered for the purpose of establishing the identity of an individual. SNPs have been considered attractive markers due to their abundance in the genome, the simplicity of multiplexing and suitability for automatic analysis and the resulting reduction in genotyping costs. Despite of their lower information content compared to microsatellites, the simplicity of multiplexing of higher number of SNP markers provide sufficient statistical power to tests for ID power and parent exclusion. The great potential of SNP markers leads to a requirement for successful high-throughput genotyping platform. This depends on coupling reliable assay chemistry with an appropriate detection system to maximise efficiency with respect to the accuracy, the speed and the cost. Several commercial systems lead this market including: DNA mass spectrometry (Sequenom), pyrosequencing (Pyrosequencing), TaqMan technology (Applied Biosystems), BeadArray technology deployed on Sentrix array matrices (Illumina) etc. Current technology platforms are able to deliver throughputs exceeding 50,000 genotypes per day, with an accuracy of >99% .These capabilities are not sufficient for the task of SNP analyses on livestock animals, because the tests are too cumbersome and require considerable resources.

Storage and transfer of data—National Animal Identification Schemes exist in several countries that are based on central databases and networks that transfer and receive data from the farms. For example, Israel's beef industry is essentially a by-product of its highly developed and centralised dairy sector. The Israel Cattle Breeders' Association runs a computerised database that is accessible via the World Wide Web (http://www.icba-israel.com/). This allows real-time reporting of data important for the herd management. In Germany, as in the whole EU, every newborn calf is identified using two ear-tags within the first seven days of life and they are registered in national data banks of the government. A "passport" is issued for every individual cattle and only animals with passports are allowed to be traded, transported, and slaughtered. All transportations have to be announced to and to be recorded by the central databank. Surprisingly, so far, there are no real and independent possibilities to monitor and control the identity of an animal or the traceability of an animal product. This would only be possible using DNA analyses.

Medigenomix www.medigenomics.de supplies traceability services and DNA fingerprinting analysis, but the samples must be sent to a central location for processing .IdentiGEN www.identigen.com, offers a full traceability service, again, the system requires that the samples be sent to a central facility. Genetic Solutions www.geneticsolutions.com.au also has a specialized system requiring centralization of sample collection and processing.

A general need exists in the agricultural and food sectors for effective and highly flexible methods and means of reversibly tracing meat products to their origins. Furthermore these methods and means must be adaptable to the individual client and situation, and should be easy to use by non specialists. Providing an easy to use, accurate DNA genotyping based tracing system which would eliminate the need to send samples to a remote centralized facility, would fulfil a long felt need. In particular, such a method for genotyping an individual head of cattle in a standard equipped laboratory would fulfil a long felt and unmet need. A system of providing accurate and reliable DNA genotyping for traceability schemes which can be implemented close to the site of interest would fulfil an unmet long felt need. An easy to use package which includes the necessary molecular biology products and data mining software for analyzing the results which could be readily used close to the site of interest by non specialist personnel would fulfil a long felt unmet need. Of course a further long felt and unmet need would be fulfilled by providing the specialized DNA primers which are required to realize the above. A high-throughput accurate genotyping platform based on SNP markers would fulfil a long felt unmet need.

National DNA based traceability schemes will increase food safety, deter cattle theft and reduce meat forgery. Additionally, full traceability will improve herd management and decrease economic losses in epidemic cases through fast identification and removal of the contamination source.

SUMMARY OF THE INVENTION

It is thus one object of the present invention to provide an efficient DNA traceability system, long-term DNA banking and genotyping by multiplexing SNP markers. The present invention discloses a method and a system for identifying animals that enables DNA marker technology to effectively and efficiently provide full traceability from the animal production and marketing chains to the system or farm of origin. This system requires SNP markers for identification of individual animals, carcasses, individual cuts of meat, and the precise origin of the animals. Collection of samples, statistically-based sampling at various control points throughout the production and distribution chain, and DNA verification systems is required to effectively implement and verify the present invention.

It is an aspect of the invention to disclose a method of genotyping an individual head of cattle. The method comprises steps of
  a. obtaining a DNA sample from an individual head of cattle;
  b. genotyping the aforementioned DNA wherein the genotyping utilizes the herein defined PCR SNaPshot protocol. The protocol comprises a first PCR step (PCR1) and a second PCR step (PCR2) further wherein the PCR1 step includes adding primers (SEQ ID No. 1-30) and/or primers extended at their 5' end with a common 10 base motif (ACGTTGGATG) to the PCR1 reaction, further wherein the PCR2 step includes adding extension primers (SEQ ID No. 31-45), and/or primers adjacent to corresponding specific SNPs;
  c. producing amplicons from a PCR1 mixture comprising the template DNA and the first primer set to yield PCR1 products;
  d. using PCR1 products as templates to a set of extension primers to yield PCR2 products;
  e. adding tails of different lengths to the PCR2 primers to enable accurate size and colour separation;
  f. stabilizing the tails of the PCR2 primers;
  g. separating the PCR2 products on a capillary sequencer;
  h. recording the results into a data bank and
  i. comparing the results with SNP profiles from the databank using data mining software to obtain data bank matching profiles.

It is a further aspect of the invention to disclose the above method wherein the step of selecting primers is performed to enable amplification in concert of PCR products in a single tube (multiplexing).

It is a still further aspect of the invention to disclose the above method wherein the step of multiplexing comprises selecting SNP markers by applying the IPLEX software (SEQUENOM, Latham et al. 2006).

It is a still further aspect of the invention to disclose the above method wherein the step of selecting said PCR1 primers comprises using GenBank sequence-files as input (Werner et al. 2004)

It is a still further aspect of the invention to disclose the above method wherein the method additionally comprises using said PCR1 products as templates to PCR2 primers and extending said PCR2 primers, with four fluorescent nucleotide-analogues in SNaPshot analysis.

It is a still further aspect of the invention to disclose the above method wherein the method additionally comprises modification of length by introducing primer tails of adenine tracts interrupted by cytosine nucleotides to the 5' end of the PCR2 primers such that a variety of extended PCR2 products are formed.

It is a still further aspect of the invention to disclose the above method wherein stabilizing the. PCR2 comprises a step of adding cytosine nucleotides to said poly-AC tails.

It is a still further aspect of the invention to disclose the above method wherein the method comprises reversibly tracing said head of cattle to an individual institution selected from a group comprising slaughterhouse, refrigeration facility, meat packing plant, meat processing plant, meat shipping plant, livestock transporter, farmers organization, market, wholesaler, distributor, quarantine facility stock yard, farm, ranch, stud farm, or pasture.

It is a still further aspect of the invention to disclose the above method wherein the method comprises tracing said individual head of cattle to a specific meat cut at a supermarket, butcher shop, restaurant or market.

It is well within the scope of the invention to provide means and methods of tracing an individual steak on a diner's plate back to the individual head of cattle.

It is a still further aspect of the invention to disclose the above method wherein the method is used in matching individual breaking table meat cuts to said individual cattle.

It is a still further aspect of the invention to disclose the above method wherein the method is used in matching retail meat cuts to individual cattle.

It is a still further aspect of the invention to disclose the above method wherein the method is used in matching fragments of meat cuts in a processed meat product such as a hamburger, sausage, salami or the like.

It is a still further aspect of the invention to disclose the above method used in the full traceability schemes defined herein.

It is a still further aspect of the invention to disclose the above method used in the partial traceability schemes defined herein.

It is a still further aspect of the invention to disclose the above method used in the concise traceability schemes defined herein.

It is a still further aspect of the invention to provide a set of DNA primers selected from a group comprising SEQ ID GenBank (Werner et al., 2004) located in genetic proximity to specific SNPs within said cattle DNA, wherein the primers are adapted to be amplified in concert thereby providing multiple PCR1 products in a single tube from a PCR1 mixture, the mixture also comprising cattle template DNA.

It is a still further aspect of the invention to provide a set of 5' extended poly-A tail PCR2 primers selected from a group consisting of SEQ ID No 31-45 further wherein the PCR2 primers are antisense to the PCR1 product templates and further extended with four fluorescent nucleotide analogues to form PCR2 products during SNaPshot analysis.

It is a still further aspect of the invention to provide a set of 5' extended poly-A tail PCR2 primers as defined above wherein the PCR2 products are separable on a capillary sequencer to provide separation data.

It is a still further aspect of the invention to provide a package for genotyping individual head of cattle, the package comprising:
a. a set of premixed DNA primers SEQ ID No. 1-30, located in genomic proximity to specific published (Werner et al 2004) SNPs, wherein the first primer set enables amplification in concert of up to 25 PCR products in a single tube from a PCR1 mixture comprising cattle template DNA.
b. and further comprising a set of premixed 5' extended stabilized tail primers selected from a group consisting of SEQ ID No. 31-45, the tail primers adapted to yield PCRII products after annealing with the PCR1 products, the PCRII products separatable on said capillary sequencer to yield SNP profiles for individual cattle and associated data mining software enabling matching of said profiles.

It is a still further aspect of the invention to provide the package with means to record, store, process and match, by means of software, the data, with predetermined SNP profiles from said data bank matching profiles.

Lastly, it is an aspect of the invention to provide the package wherein the package provides matching of the SNP profiles with the data bank profiles at an ID power ranging from about $1.11 \times 10^{-8}$ for Limousine to about $2.3 \times 10^{-10}$ for Holstein and/or Mmax ranging from about 900,822 to about 43,671,580 across breeds, while enabling parental exclusion probabilities in all breeds and detection of about 99.9% cases of incorrect parenthood, when both parental genotypes are available.

BRIEF DESCRIPTION OF THE FIGURES

In order to understand the invention and to see how it may be implemented in practice, a plurality of embodiments is adapted to now be described, by way of non-limiting example only, with reference to the accompanying drawings, in which.

FIG. 2 is a graphical representation of parental exclusion.

FIG. 3 is a graphical representation of high information content in 4 representative cattle breeds.

FIG. 6 is a schematic illustration of a computer screen graphic display.

FIG. 7 is a table showing a list of the SNP primer sequences used in the present invention.

DETAILED DESCRIPTION OF THE INVENTION

Figure 1A:
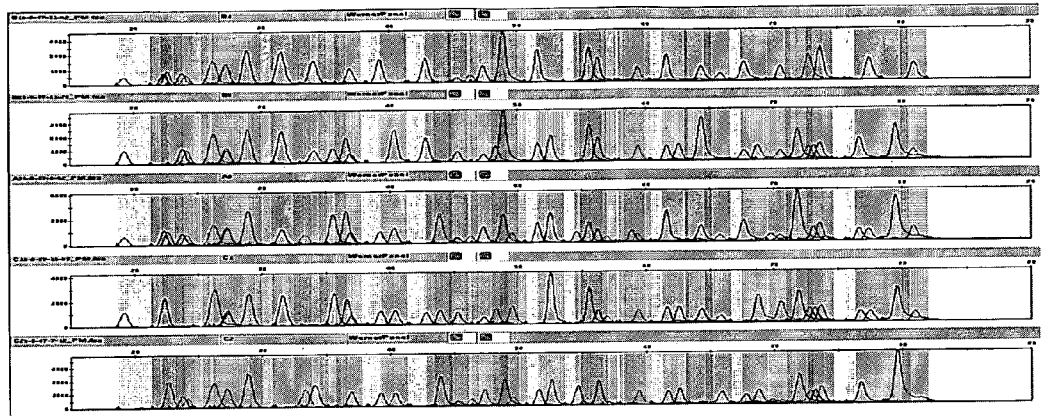
FIG. 1 is a schematic illustration of a SNP-based traceability- genotyping a 22-plex using SNaPshot.

Reference is now made to a method of genotyping an individual head of cattle. The aforementioned method comprises steps of obtaining a DNA sample from the individual and genotyping the DNA. The genotyping utilizes the herein defined PCR SNaPshot protocol. The protocol comprises a first PCR step (PCR1) and a second PCR step (PCR2). The aforementioned protocol further comprises a first PCR1 step wherein the PCR1 step includes adding primers (SEQ ID No. 1-30) and/or primers extended at their 5' end with a common 10 base motif (ACGTTGGATG) to the PCR1 reaction, further wherein the PCR2 step includes adding extension primers (SEQ ID No. 31-45), and/or primers adjacent to corresponding specific SNPs,
a) producing amplicons from a PCR1 mixture comprising the template DNA and said first primer set to yield PCR1 products
b) using PCR1 products as templates to a set of extension primers to yield PCR2 products
c) adding tails of different lengths to the PCR2 primers to enable accurate size and colour separation
d) stabilizing the tails of the PCR2 primers
e) separating the PCR2 products on a capillary sequencer
f) recording the results into a data bank and
g) comparing the results with SNP profiles from the data bank using data mining software to obtain matching profiles Reference is now made to the above defined method wherein the step of selecting primers is performed to enable amplification in concert of PCR products in a single tube (multiplexing).

Reference is now made to the aforementioned method wherein the step of multiplexing comprises selecting SNP markers by applying the IPLEX software (SEQUENOM, Latham et al. 2006).

Reference is now made to the aforementioned method wherein the step of selecting said PCR1 primers comprises using GenBank sequence-files as input (Werner et al. 2004)

Reference is now made to the aforementioned method wherein the method additionally comprises using the PCR1 products as templates to PCR2 primers and extending the PCR2 primers, with four fluorescent nucleotide-analogues in SNaPshot analysis.

Reference is now made to the aforementioned method wherein the method additionally comprises modification of length by introducing primer tails of adenine tracts interrupted by cytosine nucleotides to the 5' end of the PCR2 primers such that a variety of extended PCR2 products are formed.

Reference is now made to the aforementioned method wherein stabilizing the PCR2 comprises a step of adding cytosine nucleotides to the poly-AC tails.

Reference is now made to the aforementioned method wherein the method comprises reversibly tracing the head of cattle to an individual institution selected from a group comprising slaughterhouse, refrigeration facility, meat packing plant, meat processing plant, meat shipping plant, livestock transporter, farmers organization, market, wholesaler, distributor, quarantine facility stock yard, farm, ranch, stud farm, or pasture. It is well within the scope of the invention wherein the method comprises reversibly tracing the individual head of cattle to an individual supermarket, butcher shop, restaurant or market.

Reference is now made to disclosures of the method wherein the method is used in matching individual breaking table meat cuts to said individual cattle Reference is now made to disclosures of the method wherein the method is used in matching retail meat cuts to individual cattle Reference is now made to disclosures of the method wherein the method is used in matching fragments of meat cuts in a processed meat product such as a hamburger, sausage, salami or the like.

Reference is now made to disclosures of the method wherein the method is used in the full traceability schemes defined herein Reference is now made to disclosures of the method wherein the method is used in the partial traceability schemes defined herein Reference is now made to disclosures of the method wherein the method is used in the concised traceability schemes defined herein Reference is now made to an embodiment of the invention providing a set of DNA primers selected from a group comprising SEQ ID GenBank (Werner et al., 2004) located in genetic proximity to specific SNPs within the cattle DNA, wherein the primers are adapted to be amplified in concert, thereby providing multiple PCR1 products in a single tube from a PCR1 mixture, the mixture also comprising cattle template DNA.

Reference is now made to an embodiment of the invention providing a set of 5' extended stabilized poly-A tail PCR2 primers selected from a group consisting of SEQ ID No. 31-45, further wherein the PCR2 primers are antisense to the PCR1 product templates and further extended with four fluorescent nucleotide analogues to form PCR2 products during SNaPshot analysis.

Reference is now made to an embodiment of the invention providing the set of extended stabilized tail PCR2 primers as defined above wherein the PCR2 products are sufficiently separable on a capillary sequencer as to provide genotyping data.

Reference is now made to a package for genotyping individual head of cattle. The package comprises a set of premixed DNA primers SEQ ID No. 1-30, located in genomic proximity to specific published (Werner et al 2004) SNPs, wherein the first primer set enables amplification in concert of up to 25 PCR products in a single tube from a PCR1 mixture comprising cattle template DNA, and a set of premixed 5' extended tail PCR2 primers selected from a group consisting of SEQ ID No. 31-45. The tail primers are adapted to yield PCRII products after annealing with the PCR1 products, and the PCRII products are separable on the capillary sequencer to yield SNP profiles for individual cattle. The package additionally comprises associated data mining software enabling matching of said profiles.

Further, reference is made to the above mentioned package wherein the package is provided with means to record, store, process and match, by means of software, the data, with predetermined SNP profiles from said databank.

Lastly, reference is made to embodiments of the invention wherein the package provides matching of the SNP profiles with the databank profiles at an ID power ranging from about $1.11 \times 10^{-8}$ for Limousin to about $2.3 \times 10^{-10}$ for Holstein and/or $M_{max}$ ranging from about 900,822 to about 43,671,580 across breeds. Moreover, the aforementioned embodiments enable parental exclusion probabilities in all breeds and detection of about 99.9% cases of incorrect parenthood, when both parental genotypes are available.

In order to understand the invention and to see how it may be implemented in practice, a plurality of preferred embodiments of such a traceability system will now be described by way of non-limiting example only, with reference to the following examples:

EXAMPLE 1

Comparison Between SNaPshot and IPLEX Methods and Information Content of the SNPs Markers.

The 25-plex assay is based on SNaPshot, which is a primer extension method enabling multiplexing of several SNP markers within a single reaction. This assay allows an increase in efficiency over previous methods. In the following exemplary disclosure, the effectiveness of the 22-plex assay for traceability in meat and dairy cattle breeds is compared to IPLEX genotyping with MALDI-TOF mass spectrometry. In the following example, 22 SNP markers were shown to have a strong discriminatory power in a high number of breeds, making the system applicable for traceability.

Method and Results:

Tissue samples from eight commercial cattle breeds were collected from TypiFix™ ear-tags (Agrobiogen, Germany) through the tag locking into the animal's ear. The tissue was contained in a bar-coded chamber, which is self-sealing and contains a desiccant, which after contact, mummifies the tissue and preserves the DNA.

Extraction of DNA was performed using a one-step column system developed by Nexttec (Germany). Genomic DNA concentration was measured and 7.5 ng was used for a single reaction.

At the first step sequence data was selected from a set of 38 markers published by Werner et al. 2004 and analyzed using a MassARRAY TYPER 4.0 genotyping software for MALDI-TOF mass spectrometry by IPLEX method (SEQUENOM) in order to obtain the maximal number of SNPs that could be multiplexed in a single reaction. This software selected 23 of the 38 markers, ruling out 15 SNPs. Nine of these rejected SNPs were rejected due to mass limitation for IPLEX, and remain relevant for the SNaPshot method. Ten individuals were genotyped using the 23-multiplex in IPLEX and one SNP marker was disqualified since no polymorphism was detected.

The accuracy of the genotyping procedure was examined in 72 individuals from different cattle breeds by comparison between results obtained with IPLEX and SNaPshot 22-multiplexes. Through automatic analysis this comparison revealed 39 mismatches over 1584 single-SNP genotypes (2.46%) or 0.54 mismatches per cow. Using primers upstream to the SNP primers (Werner et al., 2004), DNA fragments were sequenced from 16 discrepancy cases. Results revealed that in all cases the sequence was unambiguously determined and matched the SNaPshot results.

At the second step the SNaPshot procedure was applied for each one of the 22 markers separately and all the products were run using ABI sequencer 310. The alleles' sizes were determined using the LIZ-120 size-standard (ABI). Repetitive runs of the same products indicated that their sizes vary up to 0.5 by between new and used capillaries. Hence, we defined 1.0 by bins around each of the expected allele sizes in the GeneMapper software (ABI). The bins were coloured according to GeneMapper defaults (FIG. 1A). Because of SNPs' binary nature, two bins were assigned for each marker.

Figure 1B:
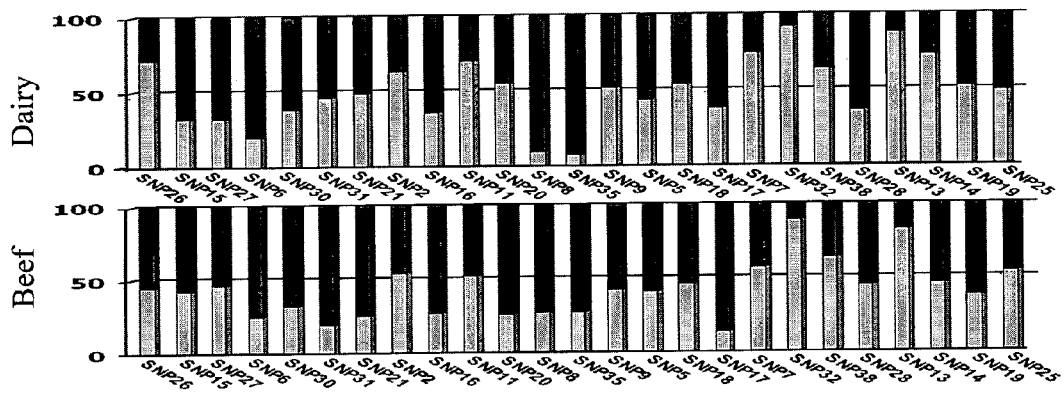
Figure 1C:
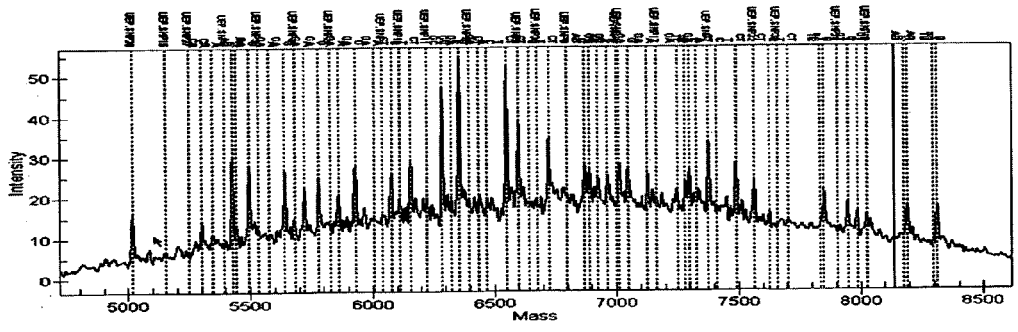

Seventeen of the second PCR primers for SnaPshot were extended by adding of poly-A tails to their 5'. This design kept intervals of at least 1.0 by between two bins with the same colour to prevent possible mistakes while minimizing the length of the whole chromatogram (FIG. 1A). All primers for the extension reaction were PAGE-purified to minimize possible artefacts. We obtained two 22-multiplexes differing only by A-tails. These two multiplexes were used to compare the two different methods: IPLEX and SNaPshot. At the third step, we added to the 22-SNaPshot panel three of the nine SNP markers that had been previously rejected by the IPLEX software. We compared the allele frequency between beef and cattle populations and concluded that the markers were informative for both (FIG. 1B). A parallel comparison of 22 SNP-multiplex unequivocally showed that the SnaPshot method is a good alternative to the IPLEX method (FIG. 1C), and the metal chip used in IPLEX is not necessary.

FIG. 1 indicates the SNP based traceability-genotyping a 22-plex using SNaPshot. The DNA extracted from 114 Dairy and beef cattle (47 and 67 individuals, respectively), from eartag samples (TypiFix™) was used as a template for simultaneous first PCR amplification using 22 primer pairs selected from a panel of 38 dairy SNPs (Werner et al., 2004).

A. An example of the allele separation and SNaPshot genotyping of five different individuals using the GeneMapper software. The chromatograms show the allele peaks and bins using the following colour code: adenine, green; cytosine, black (yellow for bins); thymine, red; and guanine, blue. SNaPshot analysis was based on second PCR amplification using the first PCR products as template, fluorescent nucleotide-analogues and extension primers with poly-A tails. The products of this second PCR were separated using an ABI capillary-sequencer.

B. Comparison of the allele frequency between two tested populations, one of dairy cattle and one population of beef cattle. For each marker the frequency of both alleles (%) is indicated in yellow and red. In the shown example, the allele marked in yellow for SNP26 was more frequent in dairy than in beef.

C. Validation of genotyping was performed for 22 SNPs using the IPLEX method. This analysis was based on second PCR amplification using the first PCR products as template, mass nucleotide-analogues and extension primers. The products of this second PCR were separated using MALDI-TOF and Sequenom mass spectrometer. A comparison of A with C shows that the graphical representation of the SNaPshot results is far easier to interpret than the IPLEX.

EXAMPLE 2

Statistical Power of the Invention for (i) Traceability and (ii) Parenthood Exclusion.

Allele frequencies of genetic markers may vary significantly between populations, thus affecting the power of genetic identification (Traceability) (Vignal et al. 2002). To evaluate the statistical power of the 25-plex assay for identity control and parentage testing, we estimated the allele frequencies in six commercial cattle breeds. A high throughput genotyping scheme was based on DNA extracted from ear-tag samples that was further used as a template for simultaneous first PCR amplification with 25 primer pairs followed by the SNaPshot analysis. A total of 274 individuals were genotyped with sample size of breeds varying between 20 and 107 individuals as indicated in Table 1. Besides a few exceptions, no family relationships were recorded among the animals.

SNPs were polymorphic in all six cattle breeds and distributions of alleles did not deviate from the Hardy-Weinberg equilibrium. Significant positive Pearson-correlation coefficients were obtained among all analyzed breeds as well as for the distribution of allele-frequency that has been previously recorded for Holstein (Werner et al. 2004). Based on the allele frequencies shown in Table 1, we calculated for each population the theoretical probability that two random individuals would have identical genotypes for all markers by chance (ID power) and the maximum number of individuals that can be resolved ($M_{max}$). The two parameters are presented in Table 1. ID power ranged from $1.11 \times 10^{-8}$ (Limousin) to $2.3 \times 10^{-10}$ (Holstein), and $M_{max}$ ranged from 900,822 to 43,671,580 across breeds at the 0.01 significance level. A traceability assay preformed on duplicated samples of 25 animals showed a perfect match of genotypes for all the 625 genotyped SNPs. This result indicates a high genotyping precision which is greater than 0.998. As an added value, the traceability system based on the 25-plex assay may assist in the herd management by better controlling the parenthood records. Parental exclusion probability was calculated referring to when both suspected parents were genotyped (Two-parent exclusion, Table 1). In all breeds, the 25-plex assay has statistical power to detect nearly all (above 99.9%) cases of incorrect parenthood, assuming that both parents' genotypes are available.

TABLE 1

SNP-allele frequencies, identity control and parenthood exclusion probabilities in six cattle breed.

| | GenBank | | | Frequency of allele 1[2] | | | | | |
|---|---|---|---|---|---|---|---|---|---|
| SNP no.[1] | Accession no. | Allele 1 | Allele 2 | Hol. N = 107 | Sim. N = 52 | Lim. N = 40 | Char. N = 31 | Ang. N = 16 | Tux. N = 20 |
| 2 | AF440368 | G | C | 0.61 | 0.72 | 0.39 | 0.79 | 0.69 | 0.45 |
| 5 | AF440372 | C | T | 0.44 | 0.56 | 0.78 | 0.69 | 0.22 | 0.45 |
| 6 | AF440381 | C | T | 0.67 | 0.81 | 0.89 | 0.90 | 0.34 | 0.92 |
| 7 | AF440377 | C | T | 0.38 | 0.15 | 0.10 | 0.08 | 0.06 | 0.16 |
| 8 | AF440369 | G | A | 0.67 | 0.79 | 0.91 | 0.73 | 1.00 | 0.63 |

TABLE 1-continued

SNP-allele frequencies, identity control and parenthood exclusion probabilities in six cattle breed.

| SNP no.[1] | GenBank Accession no. | Allele 1 | Allele 2 | Frequency of allele 1[2] | | | | | |
|---|---|---|---|---|---|---|---|---|---|
| | | | | Hol. N = 107 | Sim. N = 52 | Lim. N = 40 | Char. N = 31 | Ang. N = 16 | Tux. N = 20 |
| 9 | AF440365 | C | T | 0.46 | 0.59 | 0.24 | 0.45 | 0.13 | 0.17 |
| 11 | AJ505155 | C | T | 0.53 | 0.25 | 0.14 | 0.34 | 0.4 | 0.10 |
| 13 | AJ505160 | G | A | 0.78 | 0.14 | 0.9 | 0.89 | 0.84 | 0.68 |
| 14 | AJ505159 | C | T | 0.51 | 0.40 | 0.23 | 0.11 | 0.16 | 0.37 |
| 15 | AJ496639 | G | A | 0.49 | 0.61 | 0.8 | 0.58 | 0.47 | 0.71 |
| 16 | AJ496641 | C | T | 0.72 | 0.72 | 0.79 | 0.53 | 0.72 | 0.63 |
| 17 | AJ496635 | C | T | 0.14 | 0.38 | 0.41 | 0.42 | 0.38 | 0.50 |
| 18 | AJ496636 | G | A | 0.50 | 0.74 | 0.34 | 0.45 | 0.66 | 0.87 |
| 19 | AJ496762 | G | A | 0.46 | 0.44 | 0.46 | 0.38 | 0.50 | 0.50 |
| 20 | AJ496763 | C | T | 0.35 | 0.42 | 0.63 | 0.61 | 0.16 | 0.66 |
| 21 | AJ496765 | G | A | 0.19 | 0.42 | 0.39 | 0.34 | 0.34 | 0.34 |
| 25 | AJ496773 | C | T | 0.42 | 0.69 | 0.78 | 0.61 | 0.47 | 0.79 |
| 26 | AJ496774 | G | T | 0.61 | 0.65 | 0.63 | 0.53 | 0.47 | 0.53 |
| 27 | AJ506786 | C | T | 0.51 | 0.37 | 0.42 | 0.59 | 0.47 | 0.60 |
| 28 | AJ496776 | G | A | 0.41 | 0.28 | 0.39 | 0.30 | 0.75 | 0.24 |
| 30 | AJ496782 | C | T | 0.45 | 0.16 | 0.12 | 0.26 | 0.31 | 0.37 |
| 31 | AJ496785 | C | T | 0.56 | 0.66 | 0.66 | 0.72 | 0.5 | 0.37 |
| 32 | AJ496786 | G | A | 0.75 | 0.76 | 0.79 | 0.76 | 0.5 | 0.92 |
| 35 | AF440378 | G | C | 0.24 | 0.1 | 0.23 | 0.11 | 0.09 | 0.26 |
| 38 | AJ505157 | G | T | 0.58 | 0.62 | 0.75 | 0.59 | 0.37 | 0.60 |
| Exclusion probability | | Two-parent[3] | | 0.9995 | 0.9992 | 0.9985 | 0.9990 | 0.9986 | 0.9990 |
| ID power[4] | | | | $2.3 \times 10^{-10}$ | $1.5 \times 10^{-9}$ | $1.1 \times 10^{-8}$ | $2.5 \times 10^{-9}$ | $7.0 \times 10^{-9}$ | $2.4 \times 10^{-9}$ |
| $M_{max}$[5] | | | | $43.7 \times 10^6$ | $6.8 \times 10^6$ | $0.9 \times 10^6$ | $4.0 \times 10^6$ | $1.4 \times 10^6$ | $4.1 \times 10^6$ |

[1]SNP numbers follows Werner et al 2004.
[2]Breed names are abbreviated as follows: Hol.—Holstein; Sim.—Simmental; Lim.—Limousine; Char.—Charolais; Ang.—Angus; Tux.—Tux Cattle.
[3]The probability of exclusion, where both parents are falsely recorded (equation 3a, Jamieson & Taylor 1997).
[4]The probability that two individuals would have identical genotypes by chance (equation 1, Weller et al. 2006).
[5]$M_{max}$ is the maximum number of individuals that can be resolved (equation 3, Weller et al. 2006).

EXAMPLE 3

Graphical Representation of Parental Exclusion.

Graphical representation of parental exclusion is presented in FIG. 2.

Genetic profiles for the 25-plex were obtained, as described in example 1. Chromatograms relating analysis of individuals registered as a trio family are presented. Boxes delineate SNPs that exclude parenthood for these samples.

The paternity exclusion of the parents of a calf is illustrated in FIG. 2. The left black bordered box shows that the marker excludes both parents. Whereas the calf (FIG. 2C) shows the blue allele, both parents (FIGS. 2A, B) lack the blue allele and are homozygotic to the green allele.

The central box shows an exclusion of the sire, whilst the right hand box shows an exclusion of the dam. In summary, this example of the invention shows the exclusion of both parents by 2 SNP markers. Hence the power of the method to exclude parenthood is exemplified.

EXAMPLE 4

The Versatility of the Invention when Applied to Any Breed of Cattle.

Genotyping of hundreds of individuals from 18 breeds demonstrates the usefulness of the 25 SNP markers for genetic analyses. Allele frequencies indicate the ability to distinguish between individuals in a wide variety of breeds with the marker set demonstrates the universality and efficiency of the invention. Surprisingly even though some cattle breeds had small sample sizes (e.g. Sprinzen with 20 individuals), all 25 markers were polymorphic, testifying that the markers in the invented set are informative.

Reference is now made to FIG. 3. A graphical representation of high information content in 4 representative cattle breeds. Genetic profiles of the 25-plex were obtained, as described in example 1. For each marker the frequency of both alleles (%) is indicated in yellow and red. The following numbers of representative animals and cattle breed types were genotyped: 32 from the Charolais breed (A), 20 from the Sprinzen breed (B), 41 from the Limousin breed (C) and 52 from the Simmental breed (D).

EXAMPLE 5

Different Traceability Schemes Based on the Invention.

Reference is now made to FIG. 4. It is well within the scope of the invention to provide and disclose DNA traceability schemes (FIG. 4), especially for use in beef cattle and other meats. The present invention provides such means and methods: The term "DNA Traceability Schemes" hereinafter refers to:

1. Full DNA traceability (FDT)
2. Partial DNA traceability (PDT)
3. Concised DNA traceability (CDT)

Figure 4A:
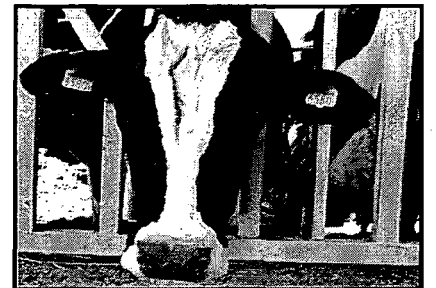
FIG. 4 is a schematic illustration of different traceability schemes based on the invention.
Figure 4B:
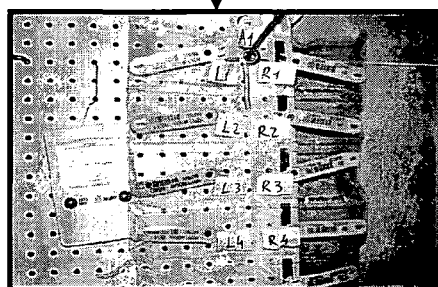
Figure 4C:
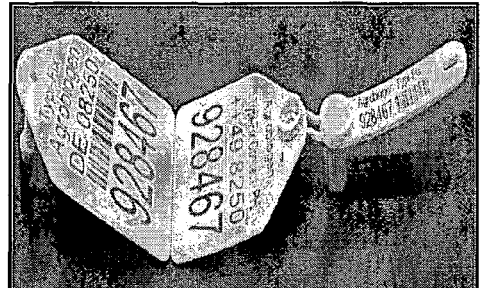
Figure 4D:
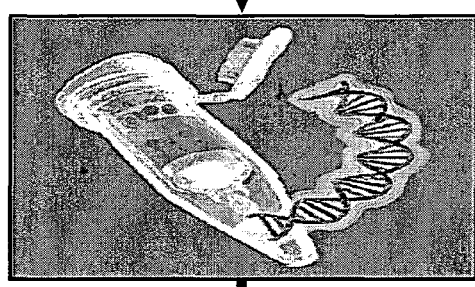
Figure 4E:
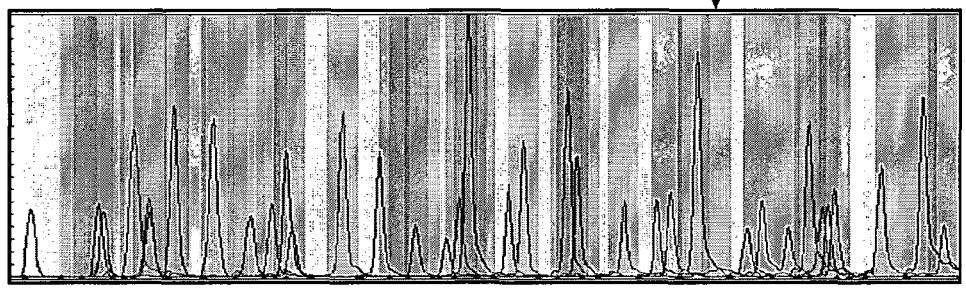

Example of a Full DNA Traceability Scheme (FDT):

All new-born cattle in a farm are ear-tagged as illustrated in FIG. 4C, and their DNA extracted as presented in FIG.

4D. All animals are genetically profiled by using the SNaPshot method as defined above in conjunction with the means, SNP markers, DNA primers selected from the group or set of premixed DNA primers SEQ ID No. 1-30, located in genomic proximity to specific published (Werner et al 2004) SNPs, stabilized DNA extension primers selected from the group (SEQ ID No. 31-45), and/or primers adjacent to corresponding specific SNPs and data mining software to achieve the genetic profile of the animal, illustrated in FIG. 4E.

Genetically profiled meat cuts in a processed meat product such as a hamburger, sausage, salami or the like, retail meat cuts, breaking table meat cuts, and individual animals are matched with the cattle profiles of the farm, reversibly tracing them back to the farm of origin The FDT can be from at least two samples per individual (eg one from the cattle itself and one from a cattle product) or far more eg from every stage of the production and distribution chain.

Example of a Partial DNA Traceability Scheme (PDT):

As illustrated in FIG. 4A, all new-borns are ear-tagged. Tissue and data banks are established as presented in FIG. 4B, and DNA is extracted on demand. Animals whose identity is required to be traced are genetically profiled by using the SNaPshot method as defined above in conjunction with the means, SNP markers, DNA primers selected from the group or set of premixed DNA primers SEQ ID No. 1-30, located in genomic proximity to specific published (Werner et al 2004) SNPs, stabilized DNA extension primers selected from the group (SEQ ID No. 31-45), and/or primers adjacent to corresponding specific SNPs and data mining software to match genetic profiles. Genetically profiled fragments of meat cuts in a processed meat product such as a hamburger, sausage, salami or the like, retail meat cuts, breaking table meat cuts and individual animals are matched and reversibly traced to the genetic profiles of the putative animal of origin, and traceability back to the farm or animal of origin is achieved, depending on the level of resolution required.

Concised DNA Traceability Scheme (CDT):

An example of such a scheme is in validation and verification checking of quality control and management procedures between the slaughterhouse and the retail outlet. All animals slaughtered in a day have DNA extracted. The animals are genetically profiled by using the SNaPshot method as defined above in conjunction with the means, SNP markers, DNA primers selected from the group or set of premixed DNA primers SEQ ID No. 1-30, located in genomic proximity to specific published (Werner et al 2004) SNPs, stabilized DNA extension primers selected from the group (SEQ ID No. 31-45), and/or primers adjacent to corresponding specific SNPs and data mining software to match genetic profiles. DNA from all products originated from that day in a retail outlet is genetically profiled. Genetically profiled fragments of meat cuts in a processed meat product such as a hamburger, sausage, salami or the like, retail meat cuts, breaking table meat cuts and individual animals are reversibly traced and matched to the slaughterhouse or animal of origin depending on the level of resolution required. Thus full traceability of the final retail product is achieved. If there is a mismatch between the animal carcass and the product, this pinpoints a possible mistake or fraud.

EXAMPLE 6

A Representative Chromatogram Depicting Separation of SNP Genotypes of the 25-Plex Using SNaPshot.

Protocol for SNaPshot method using 25 SNP markers multiplex:

Steps for this Method Application:
1. First PCR
2. Exo-SAP treatment (Shrimp Alkaline Phosphatase)
3. Second PCR
4. SAP treatment
5. Preparation of samples for running in ABI310
6. Running conditions Step's Details:

1. First PCR

Preparation Mix for First PCR:

| Reagent | Reagent concentration | Volume for one reaction (µl) |
|---|---|---|
| Nanopure water | — | 6.5 |
| PCR Buffer | x10 | 1.25 |
| MgCl2 | 25 mM | 0.65 |
| dNTPs mix | 25 mM | 0.1 |
| Genomic DNA | 7.5 ng/µl | 1.0 |
| Hotstart Taq (Qiagen) | 5 U/µl | 0.100 |
| Primer mix PCRI | — | 0.4 |
| Total: | | 10 |

Please note that it's crucial to use Hotstart Taq (Qiagen)!!!

Program for First PCR:

| Step | Temperature | Duration |
|---|---|---|
| 1 | 94° C. | 15 min |
| 2 | 94° C. | 20 sec |
| 3 | 56° C. | 30 sec |
| 4 | 72° C. | 1 min |
| 5 | Return to step2 54 times | — |
| 6 | 72° C. | 3 min |
| 7 | 4° C. | forever |

2. ExsoSAP Treatment

Preparation Mix for ExoSAP Treatment:

| Reagent | Reagent concentration | Volume for one reaction (µl) |
|---|---|---|
| PCR I Product | — | 1.5 |
| SAP Buffer | x10 | 0.5 |
| Exonuclease I | 10 U/µl | |
| SAP | 1 U/µl | 0.5 |
| Total: | | 2.5 |

A fresh mix of SAP buffer with Exonuclease I enzyme should be prepared (24|:1) and than mixing 1:1 between the $1^{st}$ mix and the SAP enzyme.

Program for ExoSAP Treatment:

| Step | Temperature | Duration |
|---|---|---|
| 1 | 37° C. | 60 min |
| 2 | 75° C. | 15 min |
| 3 | 4° C. | forever |

3. Second PCR
Preparation Mix for Second PCR:

| Reagent | Reagent concentration | Volume for one reaction (µl) |
|---|---|---|
| DNA sample | — | 1.5 |
| SNaPshot mix (ABI) | — | 2.000 |
| Primer mix PCRII | — | 2.000 |
| Total: | | 5.5 |

Program for Second PCR:

| Step | Temperature | Duration |
|---|---|---|
| 1 | 94° C. | 30 sec |
| 2 | 94° C. | 10 sec |
| 3 | 51° C. | 10 sec |
| 4 | 72° C. | 15 sec |
| 5 | Return to step2 30 times | — |
| 6 | 72° C. | 3 min |
| 7 | 4° C. | forever |

4. SAP Treatment
Preparation Mix for SAP Treatment:

| Reagent | Reagent concentration | Volume for one reaction (µl) |
|---|---|---|
| PCR II Product | — | 5.000 |
| SAP Buffer | x10 | 0.700 |
| SAP | 1 U/µl | 1.000 |
| Total: | | 6.700 |

Program for ExoSAP Treatment:

| Step | Temperature | Duration |
|---|---|---|
| 1 | 37° C. | 60 min |
| 2 | 75° C. | 15 min |
| 3 | 4° C. | forever |

5. Preparation of Samples for Running in ABI310:

| Reagent | Volume for one reaction (µl) |
|---|---|
| DNA sample | 1.2 |
| Formamide | 10 |
| LIZ120 size-standard | 0.3 |
| Total: | 11.5 |

Mix strong by vortex!

6. Running Conditions:

| Condition | |
|---|---|
| Injection time | 5 sec |
| Running duration | 16 min |

Figure 5:
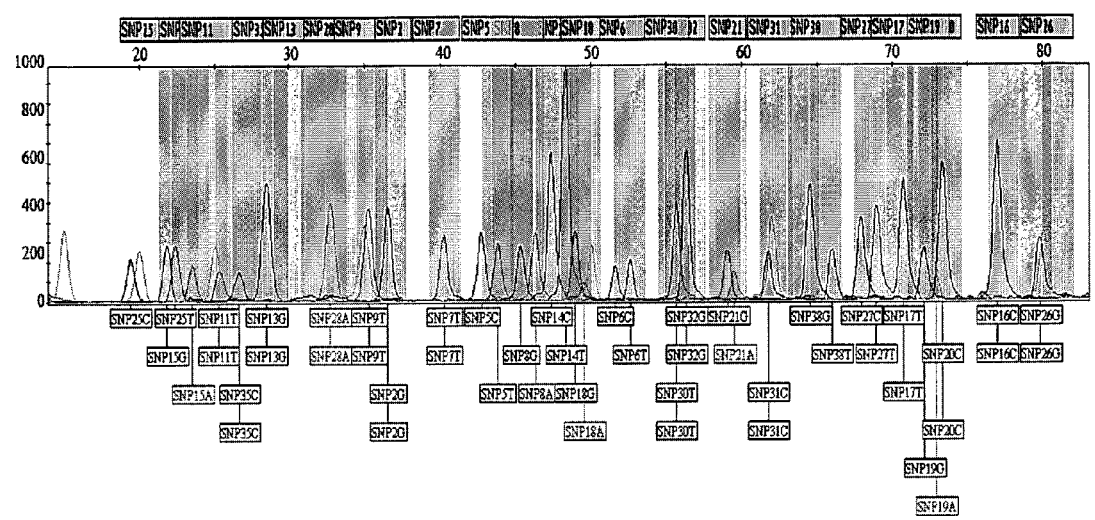
FIG. 5 is a typical chromatogram depicting separation of SNP genotypes of the 25-plex using SNaPshot.

Reference in now made to FIG. 5, which illustrates a typical chromatogram depicting separation of SNP genotypes of the 25-plex using SNaPshot.

DNA was extracted from eartag sample (TypiFix™) and was used as a template for simultaneous first PCR amplification using 25 primer pairs selected from a panel of 38 dairy cattle SNPs (Werner et al., 2004). SNaPshot analysis was based on a second PCR amplification using the first PCR products as a template, fluorescent nucleotide analogues and extension primers with poly-A tails. The PCR fragments were amplified from 7.5 ng of genomic DNA in a total volume of 10 µl with 10 µM of each dNTP, 2 mM $MgCl_2$, specific PCR primers with various concentrations (0.5-2 pmole/µl) and 0.5 U of HotStartTaq DNA polymerase (Qiagen, Inc, Valencia, Calif). The cycling profile was: initial denaturation at 94° C. for 15 min; this was followed by 55 cycles of: denaturation at 94° C. for 30 s; primer annealing at 56° C. for 30 s; and elongation at 72° C. for 1 min. Final extension was at 72° C. for 3 min. To remove remaining single-stranded primers and dNTPs, 1.5 µl of the PCR products were treated with 4 U of Exonuclease I (USB, Cleveland, Ohio) and 0.8 U of shrimp alkaline phosphatase (USB) and then incubated at 37° C. for 60 min. After enzyme inactivation at 75° C. for 15 min, SNP scoring was carried out by the single-base extension method using SNaPshot™ Kit (Applied Biosystems) according to the manufacturer's instructions. Extension reactions were carried out in a final volume of 5.5 µl, containing 1.5 µl of the purified PCR product, 2 µl of SNaPshot™ ready reaction premix and 2 µl of extension primer mix. The reaction mix was subjected to 30 cycles of 94° C. for 10 s, 51° C. for 20 s and 60° C. for 30 s. To remove unincorporated fluorescent ddNTPs, the reactions were treated with 0.5 U of shrimp alkaline phosphatase (USB) at 37° C. for 60 min and then incubated at 75° C. for 15 min. Samples were analyzed by capillary electrophoresis using an ABI 3100 genetic analyzer (Applied Biosystems) and GeneMapper software V4.0 (Applied Biosystems). An output of a GeneMapper plot demonstrating the allele separation and genotyping of an individual is presented. The chromatogram shows the allele peaks and bins using the following colour code: adenine, green; cytosine, black (yellow for bins); thymine, red; and guanine, blue. Orange peaks represent fragments of DNA size standard (GS120LIZ). Numbers on the scale above the chromatogram show size in bases. Numbers on the left indicate fluorescence intensity. Boxes denote each marker domain and allele-calls above and below the chromatogram, respectively.

EXAMPLE 7

The "Do It Yourself" (DIY) System and Genotype Mining

The current invention makes it now possible and worthwhile to establish a centralized bank for tissue samples and for recorded genotypes. All collected samples can be easily genotyped and individual profile. ("passport") can, through the embodiments of the present invention, accompany individual cattle through trade, transportation and food production. A bank of genotypes will allow the growers and the authorities to prove ownership on cattle and meat products, and also effectively prevent epidemic outbreaks. The centralized genotype data-bank can permit effective coordination of work in laboratories utilizing high throughput facilities for SNP analysis, and carry out fast action for detection and isolation of infected individuals, tissues, or their derivates. The developed full traceability system is important for the food industry and for the agricultural field in the European community.

Figures 6A, 6B:
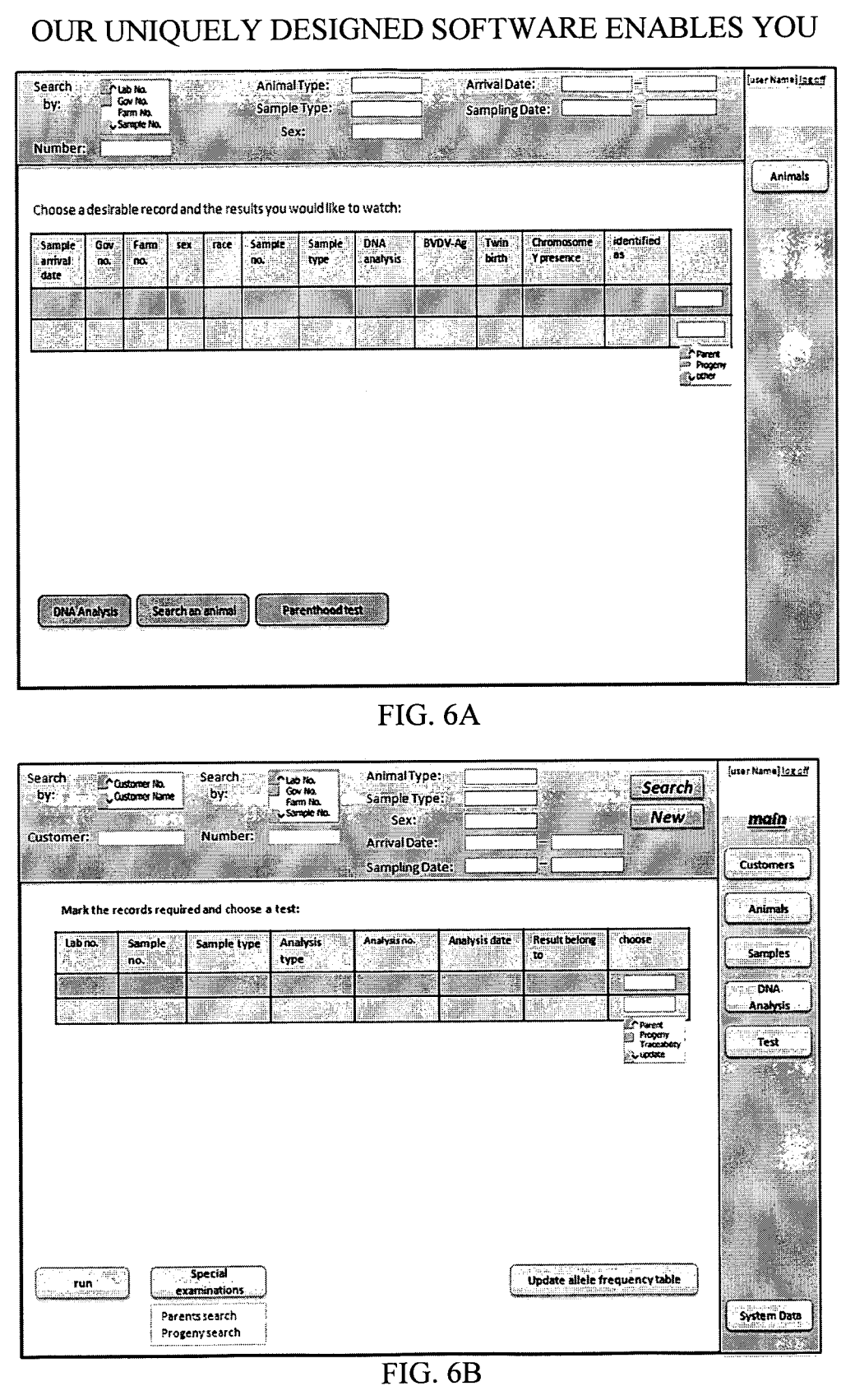

Reference is now made to FIG. 6 which schematically illustrates a computer screen graphic display of (A) the described Do It Yourself (DIY) system and (B) genotype mining.

The present invention relates to DNA traceability system at multiple levels, genotyping by multiplexing of SNP markers in one tube, data banking and genotype mining software. A novel method of genetic analysis is presented using a multiplex of a unique set of Single Nucleotide Polymorphisms (SNPs) genetic markers that effectively provide full traceability of animals from birth to consumption. The unique parameters of the present traceability system are its applicability anywhere, cost-effectiveness and its client-oriented management The invention is directed inter alia towards providing means and methods wherein a user can carry out genotyping without depending on a centralised database and laboratory. Hence, such a method can be termed a Do It Yourself (DIY) method of genotyping.

Reference is now made to FIG. 7A showing a table containing a list of the SNP primers sequences of the present invention. Seq. ID 1-15 are PCR1 forward Primers, Seq. ID 16-30 are PCR1 reverse primers and Seq. ID 31-45 are PCRII extension primers. FIG. 7B shows the 25 markers-specific loci in cattle. We define 1.0 by bins around each of the expected allele sizes in the GeneMapper software. The bins were coloured according to GeneMapper defaults.

REFERENCES

ISAG/FAO Standing Committee (2004).

Langman B. (2003) A road map to better food. *Food system insider*, March 2003.

Latham K., Stephens R., Oilier W., Crosby I., Bounce M. & Poulton K. (2006) The SEQUENOM MassARRAY technology as a high through-put SNP genotyping system. International Journal of Immunogenetics 33, 321.

Ragoussis J., Elvidge G. P., Kaur K. & Colella S. (2006) Matrix-Assisted Laser Desorption/Ionisation, Time-of-Flight Mass Spectrometry in Genomics Research. *PLoS Genet.* 2: e100.

Rohrer G. A., Freking B. A. & Nonneman D. (2007) Single nucleotide polymorphisms for pig identification and parentage exclusion. *Animal Genetics* 38, 253-258.

Weller J. I., Seroussi E. & Ron M. (2006) Estimation of the number of genetic markers required for individual animal identification accounting for genotyping errors. *Animal Genetics* 37, 387-389.

Werner F. A. O., Durstewitz G., Habermann F. A., Thaller G., Krämer W., Kollers S., Buitkamp J., Georges M., Brem G., Mosner J. & Fries R. (2004) Detection and characterization of SNPs useful for identity control and parentage testing in major European dairy breeds. *Animal Genetics* 35, 44-49.

Shirak et al., 2008. Lecture presented at AgenG conference (Crete, 2008).

The invention claimed is:

1. A method of genotyping an individual head of cattle comprising steps of:
   a. genotyping a DNA sample obtained from said individual wherein said genotyping utilizes PCR SNaPshot protocol, said protocol comprising a first PCR step (PCR1) and a second PCR step (PCR2), further wherein said PCR1 step includes adding a first primer set consisting of PCR1 primers of SEQ ID No. 1-30 to PCR1 reaction comprising said DNA sample to yield PCR1 products, and said PCR2 step includes adding extension primers consisting of PCR2 primers of SEQ ID No. 31-45 to yield PCR2 products, said genotyping is performed by multiplexing single nucleotide polymorphisms (SNPs) by amplifying in concert said PCR1 products in a single tube, followed by multiplexing said SNPs by amplifying in concert PCR2 products in the tube;
   b. producing amplicons from said PCR1 reaction comprising said DNA sample and said first primer set to yield said PCR1 products;
   c. using said PCR1 products as templates to said extension primers to yield said PCR 2 products;
   d. separating said PCR2 products on a capillary sequencer, thereby obtaining SNP profile results;
   e. recording said SNP profile results into a databank; and,
   f. comparing said SNP profile results with SNP profiles from said databank using data mining software to obtain matching profiles.

2. The method according to claim 1, wherein said step of multiplexing comprises selecting SNP markers by applying IPLEX software.

3. The method according to claim 1, wherein said step of selecting said PCR1 primers comprises using GeneBank sequence-files as input.

4. The method according to claim 1, wherein said method additionally comprises using said PCR1 products as templates to PCR2 primers and extending said PCR2 primers, with four fluorescent nucleotide-analogues in SNaPshot analysis.

5. The method according to claim 1, wherein said method additionally comprises modification of length by introducing primer tails of adenine tracts interrupted by cytosine nucleotides to the 5' end of said PCR2 primers such that a variety of extended PCR2 products are formed.

6. The method according to claim 1, wherein said method comprises steps of: forming said PCR2 products by adding poly-A tails of different lengths to the PCR2 primers to enable accurate size and color separation; and stabilizing the tails of said PCR2 primers by adding cytosine nucleotides to form poly-AC tails.

7. The method according to claim 1, wherein said method comprises reversibly tracing said head of cattle to an individual institution selected from the group consisting of slaughterhouse, refrigeration facility, meat packing plant, meat processing plant, meat shipping plant, livestock transporter, farmers organization, market, wholesaler, distributor, quarantine facility stock yard, farm, ranch, stud farm and pasture.

8. The method according to claim 1, wherein said method comprises reversibly tracing said individual head of cattle to an individual supermarket, butcher shop, restaurant or market.

9. The method according to claim 1, wherein said method is used in matching individual breaking table meat cuts to said individual cattle.

10. The method according to claim 1, wherein said method is used in matching retail meat cuts to individual cattle.

11. The method according to claim 1, wherein said method is used in matching fragments of meat cuts of a processed meat product to individual cattle, further wherein said meat product is selected from the group consisting of a hamburger, sausage and salami.

12. The method according to claim 1, wherein said method is used for full traceability of cattle from birth to consumption.

13. The method according to claim 1, wherein said method is used for partial traceability of cattle from birth to consumption.

14. The method according to claim 1, wherein said method is used for concise traceability of cattle from birth to consumption.

15. A package for genotyping individual head of cattle, said package comprising:
   a. a first premixed primer set consisting of SEQ ID No. 1-30, located in genomic proximity to SNPs, wherein said first primer set enables amplification in concert of 15 PCR1 products in a single tube from a PCR1 mixture comprising cattle template DNA and said first primer set;
   b. a set of premixed 5' extended tail primers consisting of SEQ ID No. 31-45, said tail primers configured to yield 15 PCR2 products in a single tube after annealing with said PCR1 products, said PCR2 products separable on a capillary sequencer, thereby providing SNP profile results for individual cattle; and,
   c. associated data mining software enabling matching of said SNP profile results.

16. The package according to claim 15, wherein said package is provided with means to record, store, process and match, by means of software, said SNP profile results, with a databank containing SNP profiles.

17. The package according to claim 16, wherein said package provides matching of said SNP profile results with said databank at an ID power ranging from about $1.11 \times 10^{-8}$ for Limousin to about $2.3 \times 10^{-10}$ for Holstein and/or Mmax ranging from about 900,822 to about 43,671,580 across breeds, enabling parental exclusion probabilities in all breeds, and detection of about 99.9% cases of incorrect parenthood, when both parental genotypes are available.

\* \* \* \* \*